United States Patent [19]

Guthlein et al.

[11] 4,219,336
[45] Aug. 26, 1980

[54] DIAGNOSTIC AGENT AND METHOD FOR THE DETECTION OF OCCULT BLOOD IN FECES

[75] Inventors: Werner Guthlein, Mannheim-Neckarau; Hans Wielinger; Walter Rittersdorf, both of Mannheim-Waldhof; Wolfgang Werner, Mannheim-Vogelstang, all of Fed. Rep. of Germany

[73] Assignee: Boehringer Mannheim GmbH, Mannheim, Fed. Rep. of Germany

[21] Appl. No.: 892,359

[22] Filed: Mar. 31, 1978

[30] Foreign Application Priority Data

Apr. 9, 1977 [DE] Fed. Rep. of Germany ....... 2716061

[51] Int. Cl.$^2$ ............................................ G01N 33/16
[52] U.S. Cl. ................................. 23/230 B; 252/408; 260/107; 422/56
[58] Field of Search ................ 260/97, 107; 23/230 B; 252/408; 422/56

[56] References Cited

U.S. PATENT DOCUMENTS 2,529,446  11/1950  Black ................................. 260/107 X
4,063,894  12/1977  Ogawa et al. ....................... 23/230 B
4,092,120  5/1978  Suovaniemi et al. .......... 23/230 B X

OTHER PUBLICATIONS

Auterhoff et al., Arch. Pharm., 299, 618, 1966.
Auterhoff et al., Arch. Pharm., 302, 545, 1969.

*Primary Examiner*—Arnold Turk
*Attorney, Agent, or Firm*—Sprung, Felfe, Horn, Lynch & Kramer

[57] ABSTRACT

A diagnostic agent for the detection of occult blood in feces comprising hydrogen peroxide and, as a chromogen, guaiaconic acid A, optionally with a stabilizer. The invention provides, as a novel substance, guaiaconic acid A having a specific extinction $E_{1\ cm}^{1\%}$ at 600 nm of at least 200, determined by the reaction with peroxidase and hydrogen peroxide, having infra-red bands at 1600 cm$^{-1}$ (m);
1505 cm$^{-1}$ (v.s.);
1260 cm$^{-1}$ (s;b);
1115 cm$^{-1}$ (m);
1025 cm$^{-1}$ (m); and
1200 cm$^{-1}$ (s;b)

and having an $R_F$ value of 0.45 (toluene/dioxan/glacial acetic acid; 90:25:10 v/v/v).

5 Claims, No Drawings

DIAGNOSTIC AGENT AND METHOD FOR THE DETECTION OF OCCULT BLOOD IN FECES

The present invention is concerned with guaiaconic acid A and with the preparation thereof. In different aspect, the invention provides a diagnostic agent for the detection of occult blood in feces which, as the chromogen therein, contains guaiaconic acid A with a specific extinction $E_{1\,cm}^{1\%}$ at 600 of at least 200.

The detection of occult blood in feces is important for the diagnosis of diseases of the digestive system which are accompanied by hemorrhages. Hemorrhages in the gastro-intestinal tract are usually caused by ulcers, polyps and, in particular tumors. Thus, the detection of blood in feces is an important adjunct for the early diagnosis of carcinomas of the digestive system.

For a long time, the guaiac test has been used for this diagnosis, catalysis by the peroxidate-active blood components thereby being utilized. The oxygen liberated from hydrogen peroxide is hereby transferred to a chromogen which is oxidized to a colored material and thus indicates the presence of a peroxidatively-active substance.

The guaiac test is known in several modifications. In general, it is carried out as follows: to a slurry of feces there is added hydrogen peroxide and an alcoholic solution of guaiac resin, a blue coloration indicating the presence of blood. Recently, a rapid diagnostic agent for the detection of blood in feces has been described, which comprises a filter paper impregnated with guaiac resin. This filter paper is coated with a sample of feces and, for development, an alcoholic solution of hydrogen peroxide is applied to the rear side thereof. When blood is present, a blue ring forms.

However, the use of guaiac resin for the detection of blood in feces is not without problems. In the case of the test tube test, falsely positive results are frequently found, whereas in the case of the rapid test, the detection limits depend very largely upon the other components of the faecal sample. This is due to the nature of the guaiac resin.

Guaiac resin is obtained from the heartwood of the tropical trees *Guajacum officinalic* and *Guajacum sanctum* and comprises a number of components. In principle, for the coloration by hydrogen peroxide in the presence of peroxidate-active substances, such as blood and peroxidase, two main components are responsible, namely, furoguaiacin and guaiaconic acid, especially the so-called substance A (cf. H. Auterhoff et al., Arch. Pharm., 299, 618/1966 and 302, 545/1969). In addition to a few other compounds which are present in small amounts and which can also be oxidized, there is also a comparatively large number of other component materials which do not influence the indicator reaction but which possibly inhibit it. These include, for example, guaiaretic acid, dihydroguaiaretic acid, guaiacic acid, vanillin and others.

It is, of course, well known that, in a natural product, all the components do not always occur in the same ratio so that naturally occurring guaiac resin also has a variable composition, depending upon the isolation procedure used. Furthermore, it will also be readily appreciated that, in the course of impregnation with guaiac resin, the unstable components of the mixture can also be decomposed and thus, again, can form a mixture of components of varying composition.

In the case of rapid diagnostic agents, which have recently achieved great importance, one of the main prerequisites for their practical use is that they can always be produced exactly and reproducably. However, this prerequisite was not satisfied in the case of the previously described diagnostic agents.

Thus, the problem exists of providing, by the use of definite and sufficiently pure reagents, a rapid diagnostic agent for the detection of occult blood in feces which can be produced exactly and reproducably, can be analytically tested and is also sufficiently stable.

Surprisingly, we have now found that by using guaiaconic acid A, one of the main components of crude guaiac resin, as chromogen, a rapid diagnostic agent is obtained for the determination of occult blood in feces which possesses the above-mentioned necessary properties and, furthermore, has a definite practical limit of detection.

As already mentioned above, guaiac resin consists essentially of two color-forming main components, furoguaiacin and guaiaconic acid, the structure of furoguaiacin having been unambiguously clarified by synthesis. Experiments have now shown that furoguaiacin cannot be used as a chromogen for a rapid diagnostic agent for blood in feces because it gives test papers which are much too sensitive and are also unstable.

The isolation of the other main component, guaiaconic acid, was, according to the literature, only possible by preparative thin layer chromatography, the substance being obtained in such small amounts that it could scarcely be practically considered as a chromogen for rapid diagnostic agents.

Admittedly the literature describes various attempts to isolate comparatively large amounts of guaiaconic acid but the results obtained were not very satisfactory. Thus, for example, in the thesis by J. Kuhl of the Technical High School in Braunschweig (1964, page 21), it is stated that the column chromatographic separation of guaiaconic resin with silica gel is not possible.

Surprisingly, we have now found that, in spite of this preconceived view, it is possible to separate guaiac resin by column chromatography with silica gel and to obtain guaiaconic acid in almost pure form which, without further purification, can be used for diagnostic agents for the determination of blood in feces.

Therefore, according to one aspect of the present invention, there is provided guaiaconic acid (in order to distinguish from the prior art, it is called guaiaconic acid A) which is characterized by a specific extinction $E_{1\,cm.}^{1\%}$ at 600 nm of at least 200, determined by the reaction with peroxidase and hydrogen peroxide, by infrared bands at 1600 cm$^{-1}$ (m); 1505 cm$^{-1}$ (v.s.); 1260 cm$^{-1}$ (s;b); 1200 cm$^{-1}$ (s;b); 1115 cm$^{-1}$ (m) and 1025 cm$^{-1}$ (m); and an $R_F$ value of 0.45 (toluene/dioxan/glacial acetic acid 90:45:20 v/v/v) and which is obtained by column chromatographic separation on a neutral silica gel which has been pretreated with acid, using an appropriate elution agent, for example n-heptane/ethyl acetate or toluene/acetone, under a protective gas.

As already stated above, the guaiaconic acid A thus obtained is thin layer chromatographically not quite uniform; i.e. apart from the main component, which becomes blue colored in light or with peroxidase and hydrogen peroxide, it also contains impurities which, however, because of their low concentration, can be neglected for the use thereof as a chromogen in a diagnostic agent. The guaiaconic acid A according to the present invention is amorphous and, as stated above, can be characterized by bands in the infra-red spectrum, as well as by the specific extinction and the $R_F$ value in the thin layer chromatogram (cf. Example 1 hereof).

Stating the specific extinction for the characterization has proved to be desirable since the mentioned impurities, as well as traces of solvent possibly present, considerably disturb the normal methods of analysis, such as the ultra-violet and NMR spectrum.

By the specific extinction, there is to be understood the extinction which is produced by 1 g. guaiaconic acid A in 100 ml. of solution by peroxidase and hydrogen peroxide, measurement being carried out in a 1 cm. long cuvette at 600 nm ($E_{1\ cm.}^{1\%}$).

The detailed description of the isolation of guaiaconic acid A given hereinafter in Example 1 is only a preferred embodiment of the process according to the present invention. A separation of accompanying materials of natural guaiac resin by acetone/toluene precipitation is, of course, also possible in other ways, for example by ethanol/toluene precipitation; by dissolving in glacial acetic acid and diluting with water to 30% acetic acid, taking up the precipitate in acetone/toluene (1:5 v/v) of dissolving in methyl isobutyl ketone, extracting with a sodium hydroxide/phosphate buffer of pH 13, concentrating the organic phase and diluting with toluene. Furthermore, solvent mixtures, for example xylene/acetone and methyl isobutyl ketone/toluene, can also be used as elution agents, whereby the amount ratios can also be varied. Furthermore, the throughput of guaiac resin and elution agent used can also be varied. As protective gas, it is preferable to use nitrogen or carbon dioxide.

The present invention also provides an improved diagnostic agent for the detection of occult blood in feces which is analogous to the known guaiac test but in which, instead of natural guaiac resin, as chromogen there is used guaiaconic acid A with a specific extinction $E_{1\ cm.}^{1\%}$ at 600 nm of at least 200, determined by the reaction with peroxidase and hydrogen peroxide.

Experiments have, surprisingly, shown that test papers which have been produced analogously to the known guaiac test but which, as chromogen, contained guaiaconic acid A, react with "artificial feces" (blood in water) just as sensitively as the commercially available test papers based on unpurified guaiac resin. In natural feces to which 1-3% of blood had been added, however, the papers according to the present invention reacted positively, whereas the commercially available test papers gave variable results, the limit of sensitivity, depending upon the feces varying from 1-7% and more of blood.

As already stated above, the guaiaconic acid A according to the present invention is characterized by its specific extinction. Since, in the process of isolating the guaiaconic acid, the purity of the guaiaconic acid A obtained depends upon the guaiac resin used and upon the process conditions employed, the specific extinction of the guaiaconic acid A obtained can also vary. We have found that the guaiaconic acid A in the diagnostic agent is especially suitable when its specific extinction exceeds 200. Crude guaiac resin has a value of about 100 which is due to the variable amounts of guaiaconic acid A, furoguaiacin and other unknown oxidizable components.

The guaiaconic acid A can be used in the diagnostic agent in amounts of from 40 to 250 mg. and preferably of from 50 to 150 mg. per 100 ml. of impregnation solution when it has a specific extinction of 250. In the case of other specific extinctions, the values are amended correspondingly.

In recent years, rapid tests have been used more and more in medical practice and in clinical laboratories as a diagnostic adjuvant. As a rule, they are absorbent carriers, usually papers, which have been impregnated with the reagents necessary for the detection reaction and which, after immersion into the liquid to be investigated, show a color reaction. The detection or the semi-quantitative determination of pathological body components can be carried out therewith quickly and also be untrained personnel, such as medical auxiliaries.

Apart from the actual reaction components, test papers of this type can also contain a number of additional materials, for example, buffers, wetting agents, thickening agents, protective colloids, complex formers and stabilizers, depending upon the indicator used and the purpose of the test.

Thus, the present invention also provides a test paper for the detection of occult blood in feces which, as chromogen, contains guaiaconic acid A with a specific extinction of $E_{1\ cm.}^{1\%}$ at 600 nm of at least 200. In order to prevent the papers which have been impregnated with the guaiaconic acid A from becoming blue colored due to light and/or air, it is necessary to add thereto an appropriate stabilizer. We have found that previously unknown stabilizers of the arylsemicarbazide group of compounds prevent the appearance of this blue coloration. Furthermore, we have found that, within certain limits, the sensitivity can be modified by the addition of these arylsemicarbazides.

The new stabilizers for oxidation indicators, as well as the use thereof, are described in our co-pending Patent Application Ser. No. 892,362, filed Mar. 31, 1978, the arylsemicarbazides in question being compounds of the general formula:

$$Ar\text{-}NH\text{-}NH\text{-}CO\text{-}NH_2 \qquad (I)$$

wherein Ar is an aryl radical optionally substituted by alkyl, alkoxy or halogen.

The aryl radical in the compounds (I) is preferably a phenyl or naphthyl radical. The alkyl and alkoxy radicals can contain up to 4 carbon atoms, methyl or ethyl radicals being preferred, and the halogen atom is preferably a fluorine, chlorine or bromine atom.

Furthermore, it is advantageous to impregnate the test papers with a complex former in order to form a complex with the metal ions which are usually present in papers. The salts of ethylenediamine-tetraacetic acid, especially the potassium salt, have proved to be especially suitable for this purpose, particularly since they can, at the same time, be used as buffers.

Because of the relatively large amounts of water-soluble substances present in the test papers, they can have a tendency to bleed so that it is advisable to add to the formulation thickening agents, such as methyl cellulose, gelatine or polyvinyl pyrrolidone, which can also act as protective colloids.

As wetting agents, there can be used, for example, long-chained organic sulphates or sulphonates.

For the production of the test papers according to the present invention, absorbent carriers, for example filter paper, cellulose or synthetic resin fleece, are impregnated with solutions which contain the components, preferably in mixtures of water and lower alcohols or acetone, whereafter the papers are dried.

However, it is, for example, also possible first to impregnate the complex former from water and then to impregnate the other components from organic solutions. In these papers, the most varied protection batches give the same results. In contradistinction thereto, batches of papers which have been impregnated with unpurified guaiac resin naturally show considerable variations in their sensitivity.

In contradistinction to conventional test strips, in the case of the test according to the present invention, not all of the reaction components are impregnated on to the carrier. Thus, for reasons of stability, it has been shown that the addition of hydrogen peroxide is only to take place when an immediate evaluation of the coloration is ensured. For this purpose, the detection of occult blood in feces is carried out as follows: at test strip, the production of which is described in the Examples given hereinafter, is first coated with a sample of the feces to be investigated. After drying the sample, a solution of hydrogen peroxide in alcohol is applied dropwise to the rear side of the carrier and, when blood is present in the sample, a blue coloration appears.

The following Examples are given for the purpose of illustrating the present invention:

EXAMPLE 1

Preparation of guaiaconic acid A 200 g. of ground guaiac resin are stirred into 500 ml. acetone, the resin, apart from a small amount thereof, thereby going into solution. While stirring, 3 liters of toluene are now added thereto dropwise, the precipitated material (about 60 g.) is filtered off with suction after about 30 minutes and this material is discarded. The filtrate is evaporated in a vacuum, about 160 g. of a dark brown, glassy residue being obtained. This is dissolved in 500 ml. of an n-heptane/ethyl acetate mixture (2:5 v/v), with warming, and, after cooling, it is applied to a column of silica gel (3.1 kg. silica gel, particle size 0.063-0.2 mesh), the column having a diameter of 80 cm. and a height of 1.65 m., the silica gel used having previously been freed from iron with 2 N hydrochloric acid, washed neutral with water and dried in a vacuum. Separation takes place with 7.5 liters of an n-heptane/ethyl acetate mixture (2:5 v/v) under carbon dioxide as protective gas. 150 fractions, each of 50 ml., are collected. Fractions 115-145 give, after evaporation, about 16.5 g. of a beige-colored glassy material from which about 12 g. guaiaconic acid A are obtained by recrystallization from 150 ml. xylene. It is preferable to investigate the individual fractions by thin layer chromatography since, under certain circumstances, displacements of the elution of the desired material can occur.

Thin layer chromatography

Silica gel finished plates 60 F-254 (Merck). Elution agent: toluene/dioxan/glacial acetic acid (90:25:10 v/v/v); $R_F$ value 0.45.

Spray solution

With 0.05% peroxidase and 0.5% hydrogen peroxide, the guaiaconic acid A becomes blue.

With 6% formalin and 26% sulphuric acid in water and heating for 5 minutes, guaiaconic acid A becomes brown-violet and the impurities become red to violet.

Determination of the specific extinction 4.0 g. Guaiaconic acid A are dissolved in 400 ml. 50% aqueous alcohol. 1.0 ml. of this solution, 0.5 ml. of a 3% solution of polyvinyl pyrrolidone K 90 in distilled water, 1.0 ml. of a 0.1 molar aqueous solution of hydrogen peroxide and 0.1 ml. of a 1% solution of horse radish peroxidase ($1-2\times10^3$ U/g.) in distilled water are made up to 10 ml. with distilled water. The solution is well mixed up and, after 5 to 10 minutes, measured in a 1 cm. cuvette at 600 nm.

Specific extinction = measured extinction × 1000

Infra-red bands (KBr): 1600 cm$^{-1}$ (m); 1505 cm$^{-1}$ (v.s.); 1260 cm$^{-1}$ (s;b); 1115 cm$^{-1}$ (m); 1025 cm$^{-1}$ (m); and 1200 cm$^{-1}$ (s;b).

EXAMPLE 2

Test paper for the detection of occult blood in feces

Filter paper (Schleicher & Schull 597 NF-Ind) is impregnated with the following solution and dried at 50° C.:

| | |
|---|---|
| guaiaconic acid A; $E^{1\%}_{1\ cm.}$ = 270 at 600 nm | 120 mg. |
| 1-phenylsemicarbazide | 65 mg. |
| polyvinyl pyrrolidone K 25 | 300 mg. |
| potassium EDTA buffer, pH 5.5* | 10 ml. |
| acetone | 50 ml. |
| water | ad 100 ml. |

*10 g. ethylenediamine-tetraacetic acid +4.75 g. potassium hydroxide in 100 ml. water To 30 samples of feces from different subjects there were admixed increasing amounts of blood and the samples were homogenized. Under standardized conditions, the same amounts of samples were applied to the test papers and, after drying, 2 drops of a mixture of 11 ml. perhydrol and 100 ml. ethanol were applied to the rear side of the test papers. The following Table shows the percentage of negative and positive reactions, in comparison with a commercially available test paper:

TABLE

| amount of blood added | test according to the invention | | commercially available product | |
|---|---|---|---|---|
| | negative reaction | positive reaction | negative reaction | positive reaction |
| 1% | 25 | 75 | 80 | 20 |
| 2% | 10 | 90 | 72 | 18 |
| 3% | 8 | 92 | 57 | 43 |
| 4% | 0 | 100 | 50 | 50 |
| 5% | 0 | 100 | 40 | 60 |
| 6% | 0 | 100 | 40 | 60 |

The above Table shows that the practical limit of detection (i.e. that concentration of the material to be detected with which there is obtained a positive reaction in 90 cases out of 100) is, in the case of the test papers according to the present invention, present in the case of an addition of 2% of blood. A practical limit of detection for the commercially available product cannot be given, which is confirmed by the manufacturer in his information leaflet. With aqueous blood solutions, both test papers react the same positively up to a dilution of 1:5000.

EXAMPLE 3

Test paper for the detection of occult blood in feces 60 mg Guaiaconic acid A, $E_{1\ cm.}^{1\%}$=300 at 600 nm., are dissolved in ethanol. Filter paper (Whatman No. 1)

EXAMPLE 4

140 mg. guaiaconic acid A, $E_{1\,cm.}^{1\%} = 240$ at 600 nm, and 70 mg. of one of the 1-arylsemicarbazides given in the following Table are dissolved in 100 ml. methanol. Filter paper (Whatman No. 1) is impregnated with this solution, the filter paper having been previously impregnated with a 0.4 molar buffer of ethylenediaminetetraacetic acid and aqueous sodium hydroxide solution of pH 5.5 After drying at 50° C., test papers are obtained which have practically the same properties as those described in Example 2.

The following arylsemicarbazides were used:
1-phenylsemicarbazide;
1-(o-tolyl)-semicarbazide;
1-(m-tolyl)-semicarbazide;
1-(o-methoxyphenyl)-semicarbazide;
1-(p-methoxyphenyl)-semicarbazide;
1-(m-chlorophenyl)-semicarbazide;
1-(α-naphthyl)-semicarbazide.

It will be understood that the specification and examples are illustrative, but not limitative of the present invention and that other embodiments within the spirit and scope of the invention will suggest themselves to those skilled in the art.

What is claimed is:

1. Diagnostic agent for the detection of occult blood in feces, comprising hydrogen peroxide and, as a chromogen, guaiaconic acid A, having a specific extinction $E_{1\,cm}^{1\%}$ at 600 nm of at least 200, determined by the reaction with peroxidase and hydrogen peroxide, having infra-red bands at
   1600 cm$^{-1}$ (m);
   1505 cm$^{-1}$ (v.s.);
   1260 cm$^{-1}$ (s;b);
   1115 cm$^{-1}$ (m);
   1025 cm$^{-1}$ (m); and
   1200 cm$^{-1}$ (s;b)
   and having an $R_F$ value of 0.45 (toluene/dioxan/glacial acetic acid; 90:25:10 v/v/v).

2. Diagnostic agent as claimed in claim 1 also comprising at least one adjuvant selected from buffers, wetting agents, thickening agents, protective colloids, complex formers and stabilizers.

3. Diagnostic agent as claimed in claim 1 comprising additionally a bibulous carrier for said hydrogen peroxide and guaiaconic acid A.

4. In a method for the detection of occult blood in feces, using the reaction of hydrogen peroxide with a chromogen catalyzed by peroxidate-active components of blood, by evaluation of the coloration, the improvement comprising using, as the chromogen, guaiaconic acid A, having a specific extinction $E_{1\,cm}^{1\%}$ at 600 nm of at least 200, determined by the reaction with peroxidase and hydrogen peroxide, having infra-red bands at
   1600 cm$^{-1}$ (m);
   1505 cm$^{-1}$ (v.s.);
   1260 cm$^{-1}$ (s;b);
   1115 cm$^{-1}$ (m);
   1025 cm$^{-1}$ (m); and
   1200 cm$^{-1}$ (s;b)
   and having an $R_F$ value of 0.45 (toluene/dioxan/glacial acetic acid; 90:25:10 v/v/v).

5. In a method for the detection of occult blood in feces, wherein a sample of feces is first applied to an absorbent paper which contains a chromogen and at least one adjuvant selected from buffers, wetting agents, thickening agents, protective colloids, complex formers and stabilizers, and after drying an alcoholic solution of hydrogen peroxide is applied dropwise to the rear side of the carrier and subsequently the coloration due to the reaction of the hydrogen peroxide with the chromogen catalyzed by the peroxidate-active blood components is evaluated, the improvement comprising using, as the chromogen, guaiaconic acid A, having a specific extinction $E_1^{1\%}$ cm at 600 nm of at least 200, determined by the reaction with peroxidase and hydrogen peroxide, having infra-red bands at
   1600 cm$^{-1}$ (m);
   1505 cm$^{-1}$ (v.s.);
   1260 cm$^{-1}$ (s;b);
   1115 cm$^{-1}$ (m);
   1025 cm$^{-1}$ (m); and
   1200 cm$^{-1}$ (s;b)
   and having an $R_F$ value of 0.45 (toluene/dioxan/glacial acetic acid; 90:25:10 v/v/v.

* * * * *